United States Patent
Sun et al.

(10) Patent No.: US 9,618,445 B2
(45) Date of Patent: Apr. 11, 2017

(54) OPTICAL MICROSCOPY SYSTEMS BASED ON PHOTOACOUSTIC IMAGING

(71) Applicant: National Taiwan University, Taipei (TW)

(72) Inventors: Chi-Kuang Sun, Taipei (TW);
Yu-Hung Lai, Taipei (TW);
Chieh-Feng Chang, Taipei (TW);
Szu-Yu Lee, Taipei (TW)

(73) Assignee: National Taiwan University, Taipei (TW)

( * ) Notice: Subject to any disclaimer, the term of this patent is extended or adjusted under 35 U.S.C. 154(b) by 427 days.

(21) Appl. No.: 14/100,032

(22) Filed: Dec. 9, 2013

(65) Prior Publication Data
US 2015/0160120 A1 Jun. 11, 2015

(51) Int. Cl.
*G01N 21/17* (2006.01)
*G01N 21/63* (2006.01)
(Continued)

(52) U.S. Cl.
CPC ....... *G01N 21/1702* (2013.01); *G01N 21/636* (2013.01); *G01N 29/036* (2013.01);
(Continued)

(58) Field of Classification Search
CPC ............. G01N 21/1702; G01N 21/636; G01N 29/2418; G01N 2201/06113; G01N 2201/0697; G01N 29/036; G01N 29/0654
(Continued)

(56) References Cited

U.S. PATENT DOCUMENTS

| 4,255,971 A | 3/1981 | Rosencwaig |
| 2005/0175540 A1* | 8/2005 | Oraevsky ............. A61B 5/0095 424/9.5 |

(Continued)

OTHER PUBLICATIONS

Y. Lai et al., Two-Photon Photoacoustics Ultrasound Measurement by a Loss Modulation Technique, Proc. SPIE 8581, Photons Plus Ultrasound: Imaging and Sensing 2013, 85812R (Mar. 4, 2013).
(Continued)

*Primary Examiner* — Laura Martin
*Assistant Examiner* — Rose M Miller
(74) *Attorney, Agent, or Firm* — Hannah M. Tien

(57) ABSTRACT

The present application discloses optical microscopy systems and related method that use modulation techniques and contrast agents to enable the systems to detect nonlinear photoacoustic signals with high spectrum sensitivity and frequency selectivity for imaging. A laser beam is amplitude modulated for pure sinusoidal modulation using either the loss modulation technique or the single light amplitude modulation technique. The sample used in the invention is an endogenous contrast agent by itself or is treated by at least one exogenous contrast agent to produce or enhance photoacoustic effect induced by multi-photon absorption. The modulated laser beam is focused via a focusing device onto a sample which absorbs multiple photons simultaneously and generates ultrasonic (acoustic) waves via nonlinear photoacoustic effect. The ultrasonic waves are received and transformed into electrical signals and the frequency signals within the electrical signals are detected and recorded to create images.

20 Claims, 12 Drawing Sheets

(51) Int. Cl.
*G01N 29/036* (2006.01)
*G01N 29/06* (2006.01)
*G01N 29/24* (2006.01)

(52) U.S. Cl.
CPC ..... *G01N 29/0654* (2013.01); *G01N 29/2418* (2013.01); *G01N 2201/0697* (2013.01); *G01N 2201/06113* (2013.01)

(58) Field of Classification Search
USPC .................. 73/606, 643; 600/437, 407, 476
See application file for complete search history.

(56) References Cited

U.S. PATENT DOCUMENTS

2011/0054294 A1* 3/2011 Kruger ................ A61B 5/0059
600/407
2013/0281848 A1* 10/2013 Shi ...................... A61B 5/0095
600/431

OTHER PUBLICATIONS

Y. Lai et al., Nonlinear Photoacoustic Microscopy via a Loss Modulation Technique: From Detection to Imaging, Unpublished, 2013.
P. Tian et al., "Ultrafast Measurement of Two-photon Absorption by Loss Modulation", Opt. Lett. vol. 27, No. 18, pp. 1634-1636, 2002.
K. Fujita et al., "High-resolution Confocal Microscopy by Saturated Excitation of Fluorescence", Phys. Rev. Lett. 99, 228105, 2007.
Y. Yamaoka et al., "Fine Depth Resolution of Two-photon Absorption-induced Photoacoustic Microscopy using low-frequency bandpass filtering", Opt. Express, vol. 19, No. 14, pp. 2011.
Y. Yamaoka et al., "Frequency-selective Multi-photon-excitation-induced Photoacoustic Microscopy (MEPAM) to Visualize the Cross Sections of Dense Object", Proc. of SPIE, vol. 7564, pp. 1-9, 2010.
Y. Yamaoka et al. "Enhancement of Multi-photon-excitation-induced Photoacoustic Signals by Using Gold Nanoparticles Surrounded by Fluorescent Dyes", Proc. of SPIE, vol. 7177, pp. 1-9, 2009.
N. Chandrasekharan et. al., "Non-resonant Multi-photon Photoacoustic Spectroscopy for Noninvasive Subsurface Chemical Diagnostics"., Applied Spectroscopy, vol. 58, pp. 1325-1333, 2004.
R. Shelton et. al., "Ultrahigh Resolution Photoacoustic Microscopy via Transient Absorption", Biomed. Opt. Express 1. No. 2, pp. 676-686, 2010.
S. Yoshifuku et al., Parametric Harmonic-to-fundamental Ratio Contrast Echocardiography: A Novel Approach to Identification and Accurate Measurement of Left Ventricular Area under Variable Levels of Ultrasound Signal Attenuation, Ultrasonics, vol. 46, Iss. 2, May 2007, pp. 109-118.
L. W. Wang et al., "Photoacoustic Tomography: In Vivo Imaging from Organelles to Organs", Science, vol. 335, pp. 1458-1462, 2012).
H.F. Zhang et al., "Functional Photoacoustic Microscopy for High Resolution and Non-invasive In Vivo Imaging", Nature Biotechnology, vol. 24, No. 7, 2006).
K. Maslov et al., "Optical-resolution Photoacoustic Microscopy for In Vivo Imaging of Single Capillaries", Opt. Lett. vol. 33, No. 9, pp. 929-931, 2008.
Z. Xie et al., "Pure Optical Photoacoustic Microscopy", Opt. Express, vol. 19, No. 10, pp. 9027-9034, 2011.
W. R. Zipfel et al., "Non-linear Magic: Multi-photon Microscopy in the Biosciences", Nature Biotechnology, vol. 21, No. 11, pp. 369-377, 2003.
J.B. Kiser et al., "DetermingTwo-photon Absorption Cross Section via Non-resonant Multi-photon Photoacoustic Spectroscopy" Proc. of SPIE, vol. 6759, 2007.
M.E. van Raaij et al., "Femtosecond Photoacoustics Integrated Two-photon Fluorescence and Photoacoustic Microscopy", Proc. of SPIE vol. 7564, 2010.

* cited by examiner

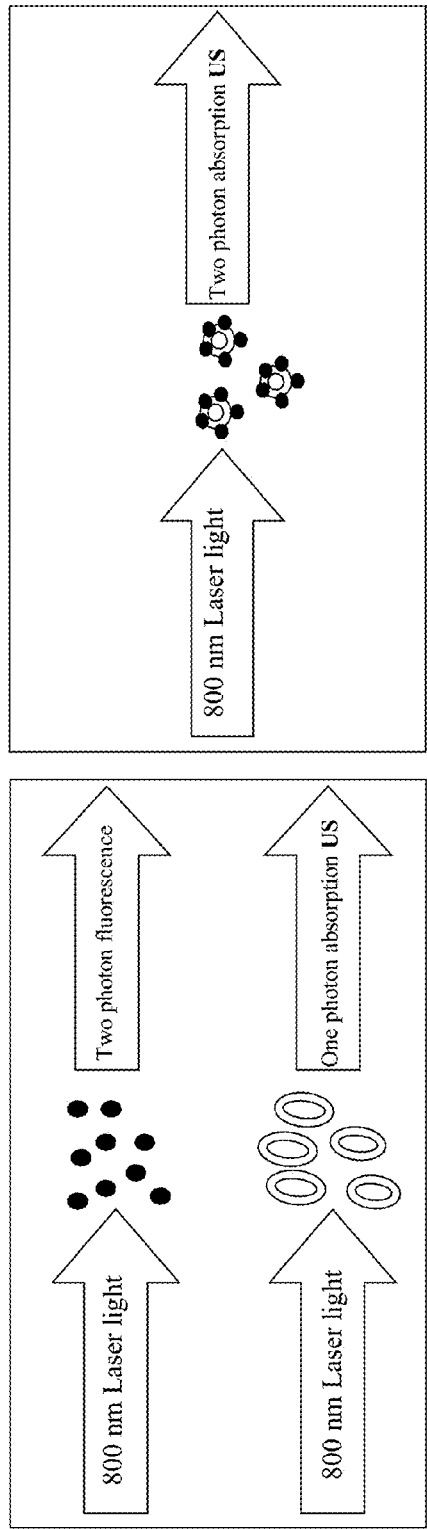
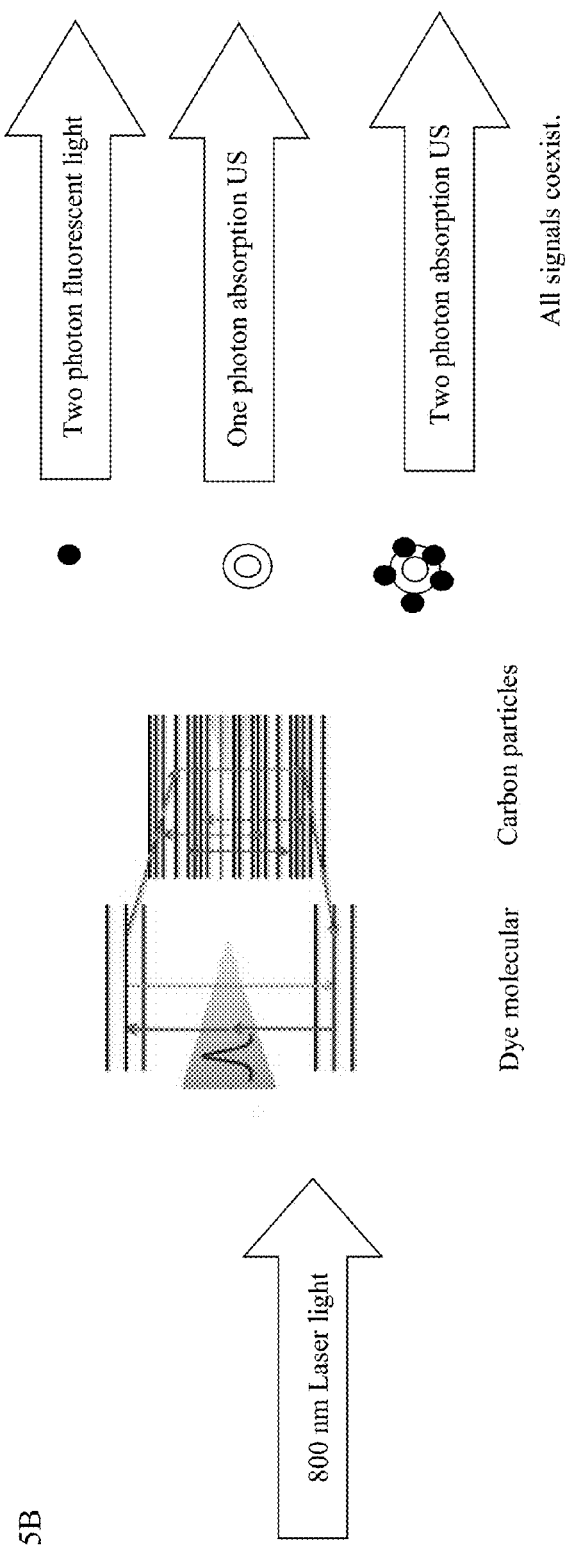
Fig. 5A
Fig. 5B

OPTICAL MICROSCOPY SYSTEMS BASED ON PHOTOACOUSTIC IMAGING

BACKGROUND OF THE INVENTION

Field of the Invention

The field of the invention relates generally to optical microscopy systems based on multi-photon photoacoustic imaging. More particularly, the present disclosure is directed to optical microscopy systems that use modulation techniques and contrast agents to enable the systems to extract nonlinear photoacoustic signals for imaging with high spectrum sensitivity and frequency selectivity.

Description of Prior Art

Photoacoustic computed tomography (PACT) and photoacoustic microscopy (PAM) are emerging technologies allowing optical absorption contrast and ultrasonic resolution to be combined in one single modality to achieve high resolution imaging at a penetration depth that is beyond optical mean free path. However, the focus of the present disclosure is on PAM, rather than PACT.

PAM can be categorized into acoustic resolution PAM (AR-PAM) and optical resolution PAM. (OR-PAM). AR-PAM weakly focuses a pulsed laser beam onto a sample to generate ultrasound by local thermal expansion, and the spatial resolution is around tens of micrometers which is within the millimeters penetration depth but beyond the existing depth limit of optical imaging modalities. The lateral resolution of AR-PAM depends on the center frequency and the numerical aperture (NA) of the ultrasonic transducer, whereas the axial resolution depends on the bandwidth of the ultrasonic transducer. High ultrasonic frequency leads to high spatial resolution. Since the acoustic attenuation coefficient is proportional to the ultrasonic frequency, the higher the ultrasonic frequency is the lower the ultrasonic penetration limit is. Generally speaking, the upper limit of the ultrasonic frequency is around 300 MHz.

To further enhance the lateral resolution of PAM, OR-PAM, which employs fine optical focusing, is proposed as an alternative. While the optical lateral resolution of OR-PAM is enhanced because of the confined photoacoustic excitation, the axial resolution is still derived primarily from the time-resolved ultrasound detection. As a result, the penetration depth of OR-PAM is only comparable to that of a conventional high-resolution optical imaging modality.

Both AR-PAM and OR-PAM heretofore focus on the single-photon excited photoacoustic effect which induces acoustic signals along the entire light path within the sample. These signals can only be ultrasonically time-resolved. The spatial resolution of AR-PAM is defined mainly by ultrasonic parameters. The lateral and axial resolution of OR-PAM are defined by optical and ultrasonic parameters, respectively. If the center frequency of the transducer is, for example, within 1 to 100 MHz, the corresponding optimal spatial resolution is limited to approximately 1.5 millimeters to 15 micrometers, and the corresponding imaging depth is limited to a few centimeters to tens of micrometers into biological tissues. It is infeasible to try to use the conventional PAM to attain imaging with spatial (i.e., both axial and lateral) resolution that is beyond the ultrasonic wavelength range when the penetration depth is limited to within millimeters.

In order to overcome the physical limitations of the conventional PAM, multi-photon photoacoustic microscopy (MPPAM), a hybrid technique combining multi-photon absorption and PAM, is recently proposed. According to nonlinear optics, multi-photon absorption is a special nonlinearity observed typically when local photon density is extremely high. For example, by focusing a pulsed laser into a sample, the high light intensity in the center of the focal area induces nonlinearity. Nonlinear microscopy such as two-photon absorption fluorescent microscopy takes advantage of this optical phenomenon to achieve sub-micron spatial resolution while using infrared photons to suppress attenuation of the tissue.

Similarly, taking advantage of the photoacoustic effect induced by multi-photon, MPPAM is capable of fine optical sectioning because the generated photoacoustic signals are well confined in the objective focal area. The spatial resolution of MPPAM almost solely depends on the dimensions of the objective focal volume. Having pure optical characteristics, MPPAM provides optical resolution rather than ultrasonic resolution and the imaging depth is within optical diffusion limit.

To induce multi-photon photoacoustic effect, it requires not only high instantaneous excitation of optical power but also efficient energy transformation in a sample from absorbed photons to phonons. Since strong single-photon absorption usually dominates the overall energy transformation process, the generated nonlinear signals are often buried in noises. Therefore, to induce multi-photon photoacoustic effect, there are two critical barriers must be overcome, detection of the weak nonlinear signals and complete separation of nonlinear signals from linear ones.

To implement MPPAM, a method used currently is to use a nanosecond laser with low repetition rate (<10 kHz) and high pulse energy (mJ/pulse) to excite the sample, and then analyze ultrasonic signals in time domain in the presence of a band-pass filtering element which increases the signal-to-noise ratio (SNR). However, several issues make this method infeasible for biomedical imaging. First, the high pulse energy causes photo-toxicity and damages to the tissue of an organism. Second, because light pulse with low repetition rate generates wide-band stimulation in frequency domain, the detection in time domain is unable to provide the spectral sensitivity and selectivity as required. Third, when linear absorption and nonlinear absorption coexist in the tissue, they tend to mix up and become indistinguishable from each other in the absence of modulation. Therefore, in order to attain high resolution and deep tissue imaging as desired, a new method which can overcome these obstacles is needed.

Prior art literatures are disclosed and discussed as follows.

Literature 1: "Thermoacoustic Microscopy" (Allen Rosencwaig et al., U.S. Pat. No. 4,255,971, 1981). This patent is the earliest patent relating to photoacoustic effect that mentions modulation. It provides an abstract concept of various modulation methods without explaining how to implement the concept. The pulsed laser, as the main excitation source of the invention, is hardly mentioned in the patent. Furthermore, it neither discusses multi-photon photoacoustic effect nor does it apply contrast agents to improve the image contrast ratio. The patent touches on an abstract concept without describing practical applications or implementations.

Literature 2: "Ultrafast Measurement of Two-photon Absorption by Loss Modulation" (P. Tian et al., Opt. Lett. Vol. 27, No. 18, 2002). This article discloses a loss modulation technique to precisely measure the efficiency of two-photon absorption.

Literature 3: "High-resolution Confocal Microscopy by Saturated Excitation of Fluorescence" (Ki. Fujiida et al., Phys. Rev. Lett. 99, 228105, 2007). This article discloses the application of the loss modulation technique in fluorescent microscopy and multi-photon fluorescent microscopy. Although the manner the signal is processed and the contrast is generated are similar to that of the present disclosure, it is different from the present invention because it acquires the image through fluorescent light detection rather than ultrasonic detection.

Literature 4: "Fine Depth Resolution of Two-photon Absorption-induced Photoacoustic Microscopy using low-frequency bandpass filtering" (Yoshihisa Yamaoka et al., Opt. Express, Vol. 19, No. 14, 2011); Literature 5: "Frequency-selective Multi-photon-excitation-induced Photoacoustic Microscopy (MEPAM) to Visualize the Cross Sections of Dense Object" (Yoshihisa Yamaoka et al., Proc. Of SPIE, Vol. 7564, 2010); and Literature 6: "Enhancement of Multi-photon-excitation-induced Photoacoustic Signals by Using Gold Nanoparticles Surrounded by Fluorescent Dyes" (Yoshihisa Yamaoka et al., Proc. Of SPIE, Vol. 7177, 2009).

Literature 4-6 describes the multi-photon-excitation-induced photoacoustic effect and the mainstream detection methods at the time. Yet, these detection methods, such as the wideband detection and the time domain analysis, cannot achieve spectral sensitivity and selectivity as desired. These methods are inherently different from the present disclosure which uses narrow-band detection and frequency domain analysis.

Literature 7: "Non-resonant Multi-photon Photoacoustic Spectroscopy for Noninvasive Subsurface Chemical Diagnostics" (Nirmala Chandrasekharan et al., Applied Spectroscopy, Vol. 58, 2004). This article discloses a novel spectroscopy based on multi-photon absorption photoacoustic effect. In this study, a nanosecond pulsed laser light is focused on a sample to induce nonlinear acoustic signal, and an unfocused ultrasonic transducer is used for detection. Moreover, the spectral absorption of exogenous absorber such as Rhodamine and tryptophan and endogenous ones inside tumors are measured and analyzed. Despite the similarity in the generation of multi-photon photoacoustic effect to MPPAM, the applications and original purposes of the spectroscopy are distinct from the microscopy of the present disclosure. Furthermore, this study uses time domain analysis with broadband detection and utilizes no modulation schemes. It indicates that there is no exact mechanism to distinguish the linear signal from the nonlinear signal, which is a core issue of MPPAM. Therefore the scope of this study is completely different from the present disclosure.

Literature 8: "Ultrahigh Resolution Photoacoustic Microscopy via Transient Absorption" (Ryan L. Shelton et. al., Biomed. Opt. Express 1. No. 2, 2010). This article discloses a square wave modulation on a light source. The system uses two modulators in the chopping mode to modulate a pump beam and a probe beam, respectively. It then uses an objective lens to focus the two beams into a sample, and measures the transient response of the induced photoacoustic signal by an ultrasonic probe. The system also integrates the signal with respect to the difference frequency and sum frequency. However, the manner of its modulation is different from that of the present disclosure, which uses pure sinusoidal modulation. In addition, the signal extraction method of this study is a pump-probe technique, instead of a loss-modulation technique. Finally, this study fails to address the problems incurred during the square wave modulation, the induced even harmonics in particular when the modulator operates in the non-sinusoidal modulation mode.

SUMMARY OF THE INVENTION

The present invention provides optical microscopy systems. The system includes a pulsed light source configured to emit at least one laser beam, at least one light modulation module configured to amplitude modulate the beam envelop of the laser beam for pure sinusoidal modulation. A focusing device is configured to focus the modulated laser beam onto a sample which is an endogenous contrast agent or is treated by at least one exogenous contrast agent so as to be excited to generate nonlinear photoacoustic waves in the sample in response to the modulated laser beam. An ultrasonic transducer module is used to receive, transform nonlinear photoacoustic waves into electrical signals and to detect frequency signals within the electrical signals. Finally, a scanning device is provided to move either the sample or the focused beam so as to scan, record, map, and process the intensity of the signals received from the ultrasonic transducer module to create images of the sample.

BRIEF DESCRIPTION OF THE DRAWINGS

The embodiments described herein may be better understood by referring to the following description in conjunction with the accompanying drawings.

FIG. 1A illustrates how acoustic waves are generated by single-photon absorption process. FIG. 1B illustrates how acoustic waves are generated by multi-photon absorption, including two-photon absorption.

FIG. 3 are block diagrams of optical microscopy systems according to two embodiments of the present disclosure using the loss modulation technique.

FIG. 5A is a schematic diagram showing the effects of carbon particles, fluorescent dye molecules, and an exogenous contrast agent produced by mixing carbon particles with fluorescent dye molecules. FIG. 5B is a schematic diagram showing the energy band structure of the contract agent, a mixture of fluorescent dye molecules and carbon particles.

DETAILED DESCRIPTION OF THE INVENTION

While the making and using of various embodiments of the present disclosure are discussed in detail below, it should be appreciated that the presently described embodiments provide many applicable inventive concepts that may be embodied in a wide variety of contexts. The embodiments discussed herein are merely illustrative of exemplary ways to make and use embodiments of the present disclosure and do not delimit the scope of the present disclosure.

To facilitate the understanding of the presently described embodiments, a number of terms are defined below. Terms defined herein have meanings as commonly understood by a person of ordinary skill in the areas relevant to aspects of the disclosure. Terms such as "a," "an," "the," and "said" are not intended to refer to only a singular entity, but include the general class of which a specific example may be used for illustration and are intended to mean that there are one or more of the elements. The terms "comprise," "have," "include," "contain," implies inclusion inside or drafting in an open way, which will not exclude unquoted elements or steps additionally.

As used herein, the term "narrow band detection" refers to detection of a pulse response in a narrow frequency band, or detection of a time-averaged integral signal with respect to a particular frequency.

As used herein, the term "frequency signal" refers to a single-photon absorption signal, a two-photon absorption signal, or a multi-photon absorption signal. The power dependency of the single-photon absorption signal is linear (i.e., the signal intensity is proportional to the input power). The power dependency of the two-photon absorption signal or multi-photon absorption signal is nonlinear (i.e., the signal intensity is proportional to the second power or the higher power of the input power). If the photon absorption signal is saturated, the frequency signal is a nonlinear saturation signal, and, empirically, the power dependency of the signal is approximately proportional to the square root of the input power.

Figure 1A:
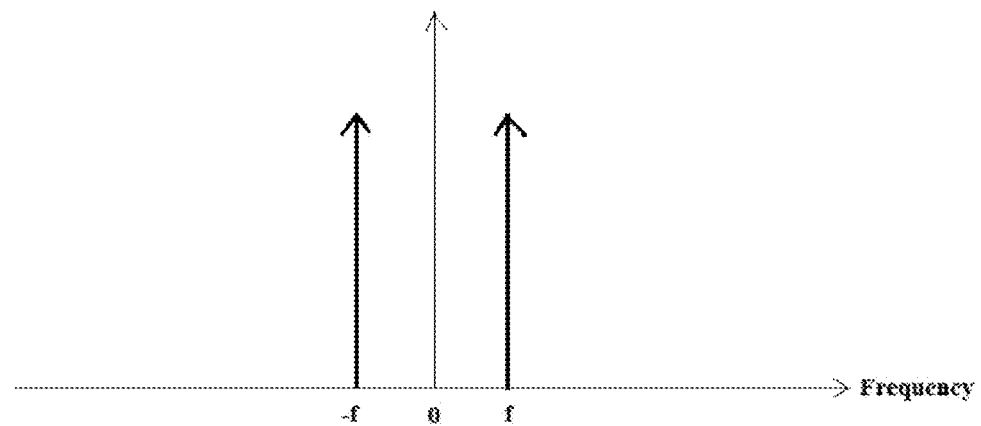
FIG. 1A and FIG. 1B illustrate the separation of a linear signal from a nonlinear signal.
Figure 1B:
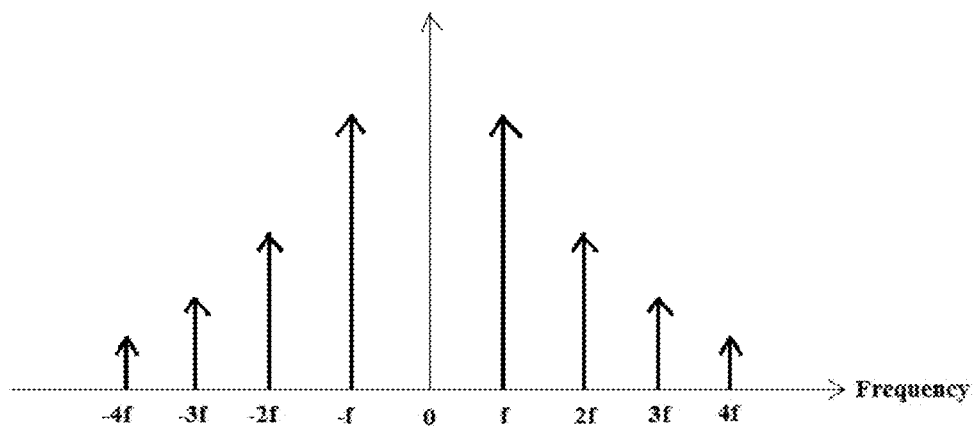

It has been demonstrated that the envelope of a laser beam may be amplitude modulated at a particular frequency for pure sinusoidal modulation using modulation techniques, and multi-harmonics may only be generated by nonlinear phenomena. (Y. Lai et al., Two-Photon Photoacoustics Ultrasound Measurement by a Loss Modulation Technique, Proc. SPIE 8581, Photons Plus Ultrasound: Imaging and Sensing 2013, 85812R, 2013. Y. Lai et al., Non-linear Photoacoustic Microscopy via a Loss Modulation Technique: from Detection to Imaging, unpublished. These two articles are hereby incorporated by reference in its entirety.) When the envelop of a laser beam is amplitude modulated for pure sinusoidal modulation at a fundamental frequency, for example f, the acoustic waves generated at the fundamental frequency after a material absorbs the amplitude modulated laser beam through a single-photon absorption process are shown in FIG. 1(A). No acoustic waves is generated at 2f, 3f, or higher harmonics of the fundamental frequency. However, as shown in FIG. 1(B), when a material absorbs the amplitude modulated laser beam through two-photon or multi-photon absorption process, acoustic waves are generated at second harmonics of the fundamental frequency, 2f, or at even higher harmonics of the fundamental frequency, such as 3f, 4f, etc. Therefore, the photoacoustic waves, i.e., the ultrasonic signals, induced by two-photon absorption or multi-photon absorption can be detected by extraction of multi-harmonics of the fundamental frequency (including the second harmonics of the fundamental frequency) with high spectrum sensitivity and frequency selectivity.

Accordingly, embodiments of the present disclosure provide optical microscopy systems exploiting nonlinear photoacoustic effect induced by two-photon or multi-photon absorption in conjunction with ultrasound detection.

Specifically, embodiments of the present disclosure use a pulsed light source 101 to emit a laser beam/pulse with high peak power and high repetition rate. The beam envelop of the laser beam is amplitude modulated by a light modulation module 102 at a fundamental frequency using a loss modulation technique or a single light amplitude modulation technique for pure sinusoidal modulation (i.e., the harmonics to fundamental ratio, HFR is as small as −30 dB. (See S. Yoshifuku et al., "Parametric Harmonic-to-fundamental Ratio Contrast Echocardiography: A Novel Approach to Identification and Accurate Measurement of Left Ventricular Area under Variable Levels of Ultrasound Signal Attenuation, Ultrasonics, Vol. 46, Iss. 2, May 2007, pp. 109-118). A focusing device 103 is used to focus the modulated laser beam onto a sample 20 so as to cause periodic heating inducing nonlinear absorption to generate photoacoustic waves (i.e., ultrasonic signals) within the focal spot through thermal relaxation process. Therefore, the optical contrast of the present disclosure solely comes from optical absorbers and the resolution is defined solely by the optical components of the invented system. The sample 20 itself serves as an endogenous photoacoustic contrast agent or is treated by at least one exogenous photoacoustic contrast agent to produce and/or enhance photoacoustic effects induced only by multi-photon (nonlinear) absorption (including two-photon absorption). The ultrasonic signals are received and transformed into electrical signals by an ultrasonic transducer module 104. The multi-harmonics of the fundamental frequency within the electrical signals are extracted with high sensitivity and selectivity by the ultrasonic transducer module 104 and to create images of the sample 20 by a scanning device 105. The signal detection of the present disclosure is based on frequency domain analysis, which focuses on the characteristics of the signal in frequency domain only. Mirrors 1032 are installed along the light path as required to direct the laser beam. An embodiment of the present disclosure has achieved approximately a spatial resolution of 1 μm, and a maximum penetration depth of approximately 1 mm.

In some embodiments of the present disclosure, the frequency range of the acoustic signal is between 20 kHz to 200 MHz. The wavelength of the ultrasound corresponding to the low frequency band from 200 kHz to 2 MHz is relatively long. The long wavelength ultrasound is suitable for ultra-deep imaging because of its low optical excitation efficiency rate and small attenuation value. The wavelength of the ultrasound corresponding to high frequency band from 2 MHz to 20 MHz is relatively short. The short wavelength ultrasound is suitable for higher resolution scanning in shallow layer because of its high optical excitation efficiency rate and large attenuation value.

Figure 2A:
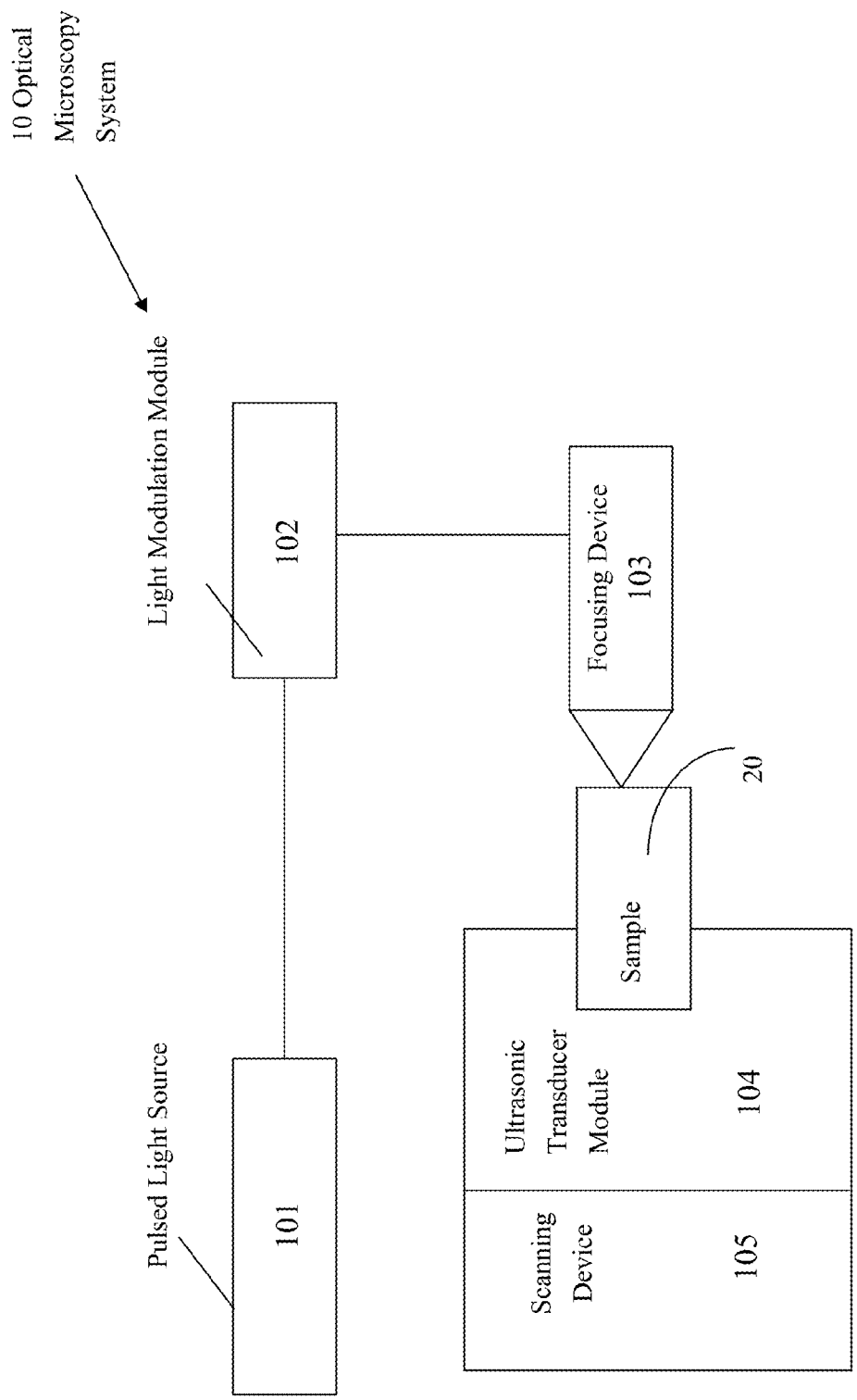
FIG. 2A is a block diagram of an optical microscopy system according to one embodiment of the present disclosure employing a scanning device configured and positioned to move the sample to be imaged for imaging.
Figure 2B:
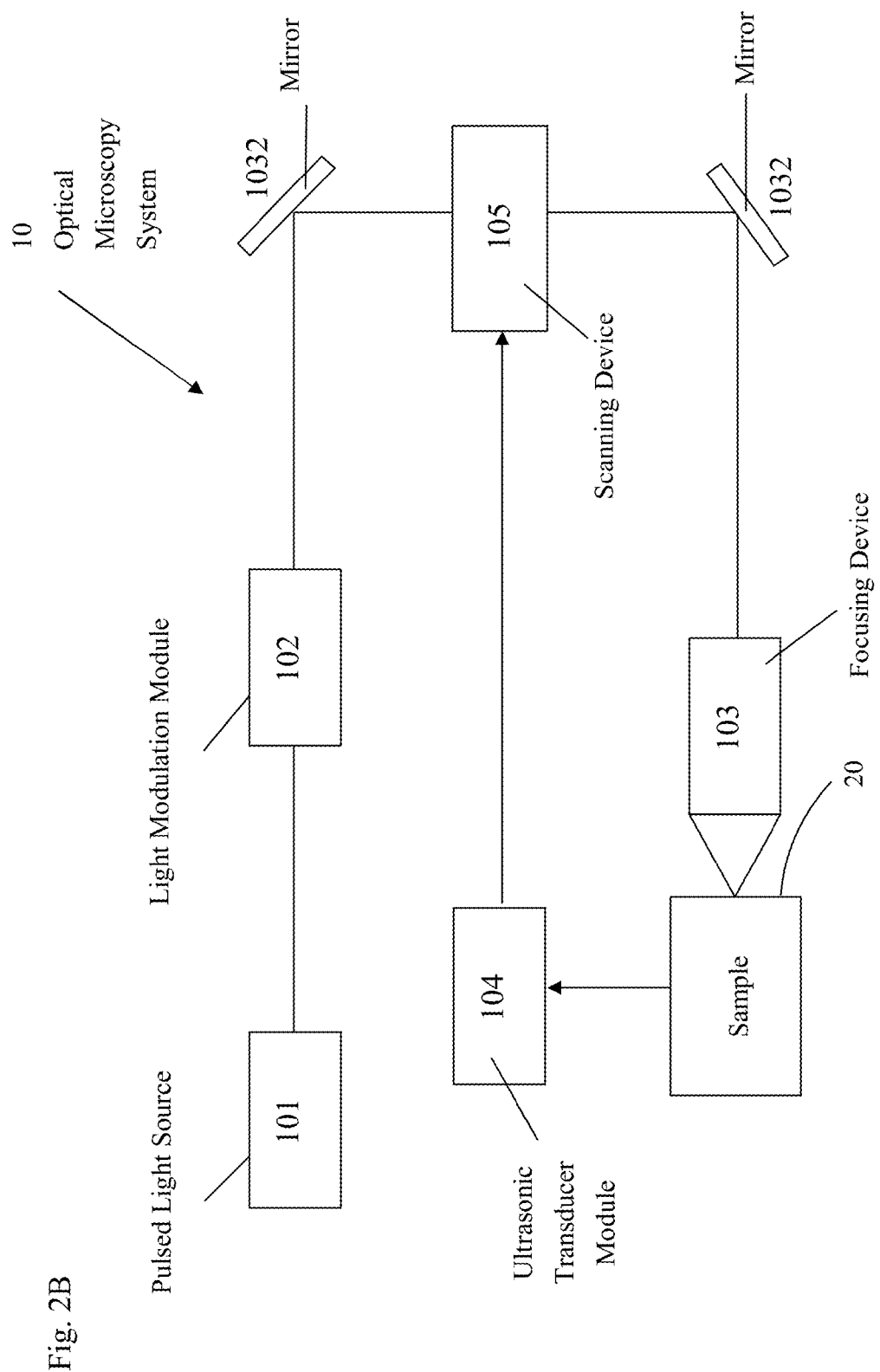
FIG. 2B shows a similar system that employs a scanning device configured and positioned to move the focused laser beam for imaging.

FIG. 2A is a block diagram of an optical microscopy system according to one embodiment of the present disclosure. A pulsed light source 101 emits at least one laser beam/pulse. The laser beam passes through a light modulation module 102 to be amplitude-modulated for pure sinusoidal modulation. The modulated laser beam is then focused onto a sample 20 via a focusing device 103 to cause periodic heating which induces nonlinear absorption and nonlinear photoacoustic effect. The sample 20 is an endogenous contrast agent which causes or enhances nonlinear photoacoustic effect by itself or is treated by at least one exogenous contrast agent for nonlinear photoacoustic effect. Ultrasonic signals generated by nonlinear photoacoustic effect and received, transformed into electrical signals by an ultrasonic transducer module 104. The multi-harmonics of the fundamental frequency (including the second harmonics of the fundamental frequency) within the electrical signals are extracted and transferred from the ultrasonic transducer module 104 to the scanning device 105 to be received, recorded and processed for imaging. The scanning device 105 comprises a 3D scanning stage and a data processing unit for 2D or 3D imaging of the sample 20 at different depth and for synchronizing the scanning device 105 and the ultrasonic transducer module 104 in order to map a recorded signal intensity to the corresponding pixel. Further, the scanning device 105 is configured and positioned to move either the sample or the focused laser beam for imaging as shown respectively in FIG. 2 (A) and FIG. 2 (B). When the scanning device 105 is configured and positioned to move the focused laser beam it is suitable for applications inside body cavities such as endoscopy. In other embodiments of the present disclosure, the data processing unit 1022 may be an independent unit, separate from the scanning device 105.

In some embodiments of the present disclosure, the focusing device 103 and the ultrasonic transducer module 104 are assembled on the same side (reflection mode), on the opposite side (transmissive mode), or by the side (orthogonal mode) to accommodate various diagnostics conditions.

Some embodiments of the present disclosure employ a femtosecond laser or a picosecond laser, which has low pulse energy (<1 µJ) and high repetition rate (>20 kHz), as the pulsed light source 101. In one embodiment of the present disclosure, the pulse energy of the pulsed light source is 5 nJ while the pulse repetition rate is as high as 80 MHz. In other embodiments of the present disclosure, a plurality of pulsed light sources, which can be confined to or concentrated in a small volume within an object, may be used.

Embodiments of the present disclosure employ at least one ultrasonic transducer module 104. The ultrasonic transducer module 104 is configured to receive and transform ultrasonic signals into electrical signals, and then to detect frequency signals within the electrical signals. In one embodiment of the present disclosure, the ultrasonic transducer module 104 is an immersion-type ultrasonic transducer. In other embodiments of the present disclosure, a plurality of ultrasonic transducers may be used. Such ultrasonic transducers include, but are not limited to, ultrasonic probes, ultrasonic arrays, piezo-electric ceramic materials (e.g., PZTs), optical resonance cavities, or ring cavities.

For laser beams emitted from the pulsed light source 101 to be amplitude-modulated for pure sinusoidal modulation, embodiments of the present disclosure employ at least one light modulation module 102. In one embodiment of the present disclosure, an acousto-optical modulator (AOM) is used. In other embodiments of the present disclosure, a plurality of light modulation modules may be used. Such light modulation modules include, but are not limited to, acousto-optical modulators, electro-absorption modulators, electro-optical modulators, magneto-optical modulators, liquid crystal space modulators, or a combination thereof.

Figure 3A:
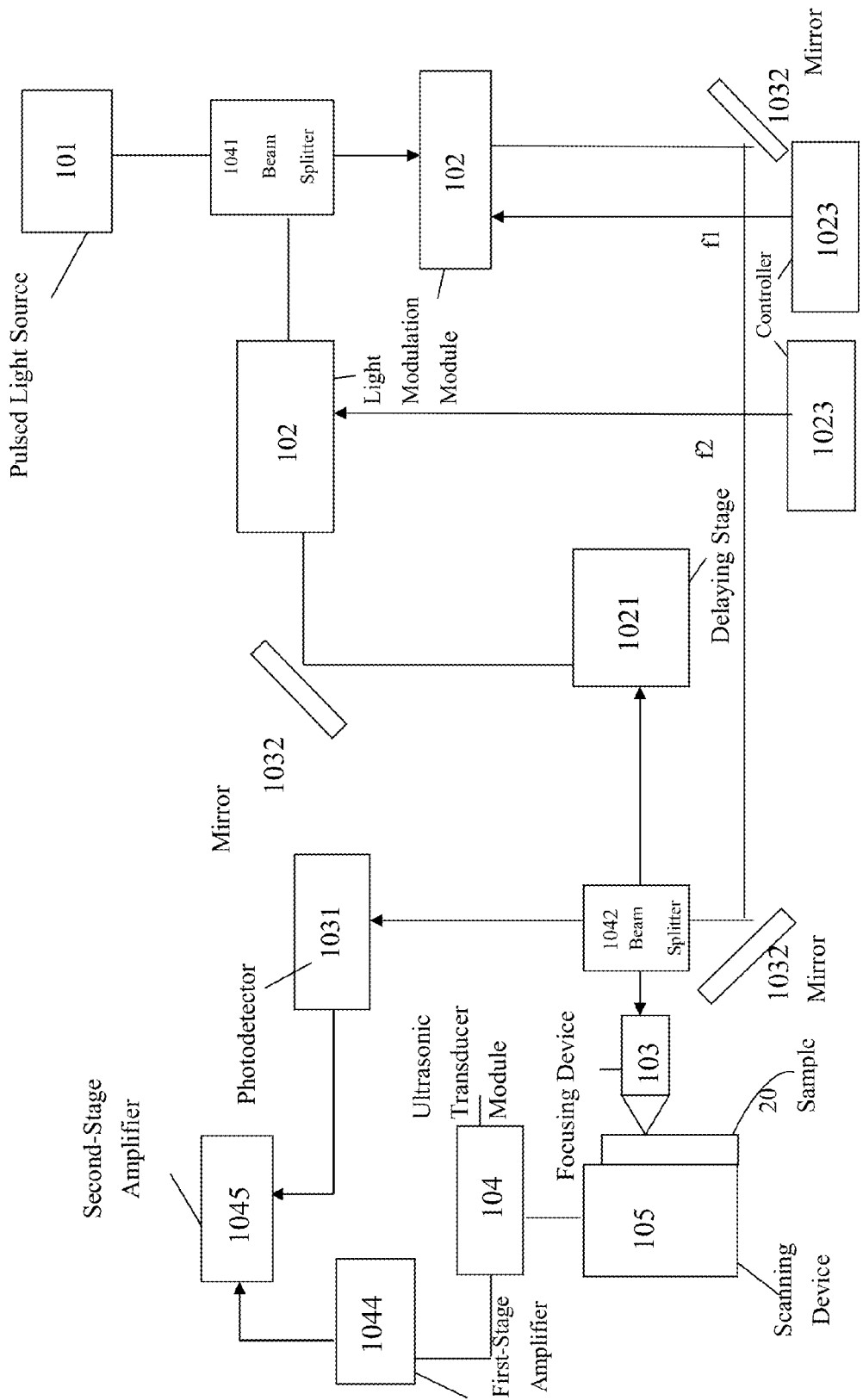
FIG. 3A is a diagram of an optical microscopy system according to one embodiment of the present disclosure that uses two light modulation modules.

To amplitude modulate a laser beam for pure sinusoidal modulation, some embodiments of the present disclosure use a loss modulation technique (the beating technique). In these embodiments, as shown in FIG. 3A, two light modulation modules 102 are installed respectively in two light paths. Both light modulation modules 102 are operated in a continuous wave (CW) mode for frequency modulation. The laser beam emitted from the pulsed laser light source 101 is split into two beam arms by a beam splitter 1041. Each beam arm then individually and separately passes through one of these two light modulation modules 102. The frequencies of these two light modulation modules are modulated slightly different by a controller 1023. When these two beam arms are spatially and temporally recombined by passing through another beam splitter 1042, the frequency difference between these two beam arms causes a beating, which results in a pure sinusoidal waveform on the beam envelope. The frequencies of the light modulation module may be adjusted by a controller 1023. In one embodiment of the present disclosure, one of the light paths is adjusted via a delay stage 1021 to ensure the travel distance between the two beam arms is the same.

Figure 3B:
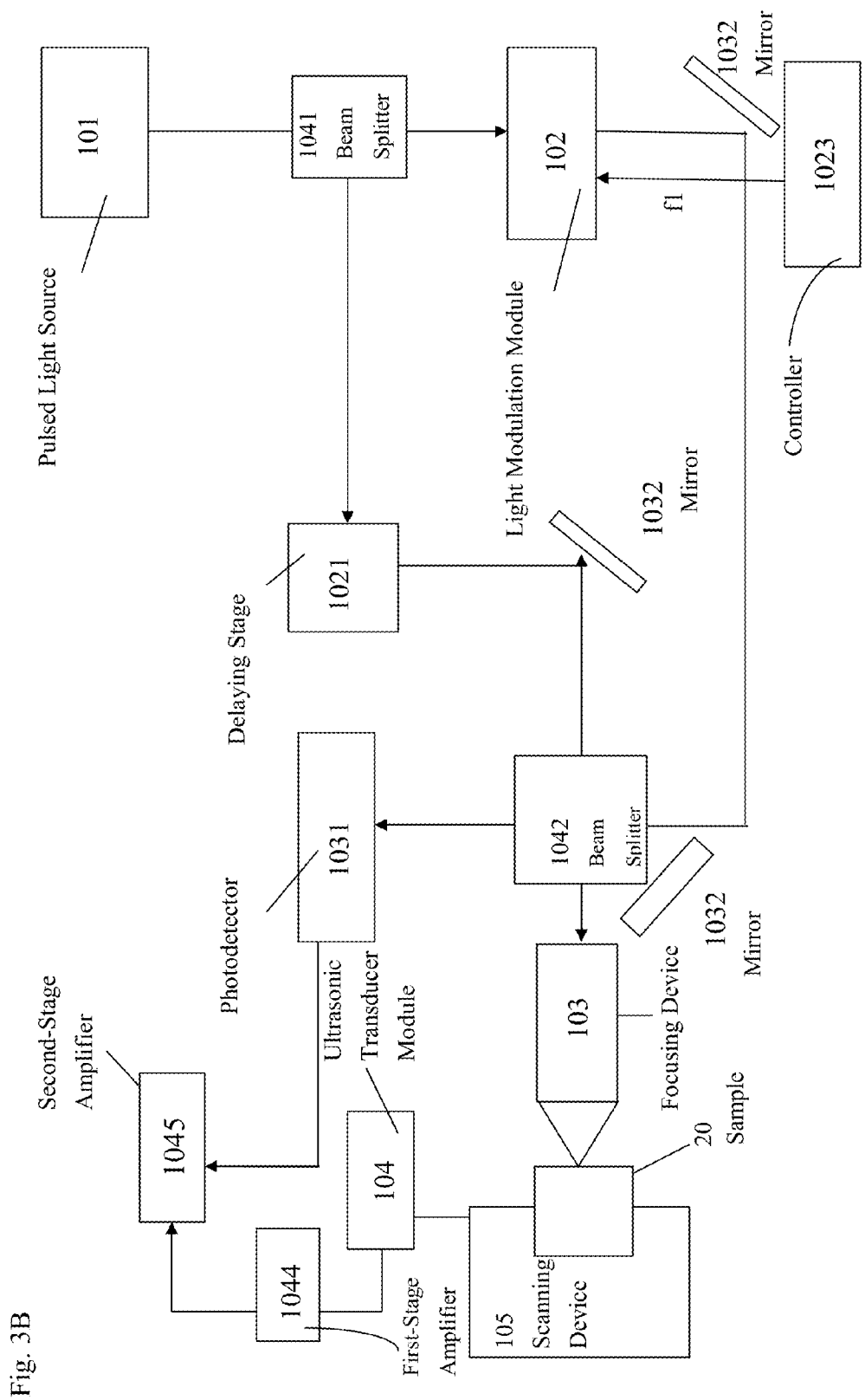
FIG. 3B is a diagram of an embodiment of the present disclosure that uses only one light modulation module.

In other embodiments of the present disclosure that use the loss modulation technique, as shown in FIG. 3B, only one light modulation module 102 is installed in one of the two light paths. The light modulation module 102 is operated in a continuous wave (CW) mode for frequency modulation. The laser beam is split into two beam arms by a beam splitter 1041. Only one beam arm passes through the light modulation module 102 which modulates the frequency of the beam arm. When these two beam arms are spatially and temporally recombined by passing through another beam splitter 1042, the frequency difference between these two beam arms causes a beating, which results in a pure sinusoidal waveform on the beam envelope. The frequencies of the light modulation module 102 may be adjusted by a controller. In one embodiment of the present disclosure, one of the light paths is adjusted via a delay stage 1021 to ensure the travel distance between the two beam arms is the same.

As shown in FIG. 3A and FIG. 3B, some embodiments of the present disclosure using the loss modulation technique comprises an ultrasonic transducer module 104 which has a frequency response covering only the desired harmonics of the fundamental frequency, and the fundamental frequency and all other harmonics are excluded from the response region. In these embodiments, the recombined beam from the beam splitter 1042 passes through a focusing device 103 for photoacoustic excitation and the ultrasonic transducer module 104 serves as a frequency filter to extract specific photon absorption photoacoustics.

As shown in 3A and 3B, some embodiments of the present disclosure using the loss modulation technique comprise an ultrasonic transducer module 104 having a wide frequency response covering multiple harmonic frequencies, a first-stage amplifier 1044, being connected to the at least one ultrasonic transducer module 104 and capable of generating an internal reference signal, and a second-stage amplifier 1045, being connected to the first-stage amplifier 1044. The second-stage amplifier 1045 used in this embodiment is for receiving and narrow band detection of the frequency signals of the initial electrical signals (f or 2f).

As shown in FIG. 3A and FIG. 3B, one embodiment of the present disclosure using the loss modulation technique further comprises a photodetector 1031. There are two recombined beams coming from the beam splitter 1042. One recombined beam is for photoacoustic excitation and the other recombined beam is sent to the photodetector 1031 which transforms the recombined beam into an electrical signal and sends this signal as a reference to the second-stage amplifier 1045.

As shown in FIG. 3A and FIG. 3B, some embodiments of the present disclosure using the loss modulation technique further comprises a first-stage amplifier 1044 for amplifying the initial electrical signal transformed from an ultrasonic wave by the ultrasonic transducer module 104 and the amplified signal is sent from the first-stage amplifier 1044 to the second-stage amplifier 1045.

In one embodiment of the present disclosure using the loss modulation technique, the first-stage amplifier 1044 is a preamplifier. In other embodiments of the present disclosure, a plurality of amplifiers may be used. Such amplifiers include, but are not limited to, low noise preamplifiers, high linear preamplifiers, optical spectrum analyzers, or radio frequency spectrum analyzers. In one embodiment of the present disclosure using the loss modulation technique, the second-stage amplifier 1045 is a lock-in amplifier. In other embodiments of the present disclosure, a plurality of amplifiers may be used. Such amplifiers include, but are not limited to, frequency analyzing means, or oscilloscopes.

The equation of the fundamental frequency (or the beating frequency) of the modulated laser beam is min ($|f_1 \times Order_1 - f_2 \times Order_2 + n \times f_R|$). The fundamental frequency may be calculated by the following formula: "the product of the modulation frequency $f_1$ and the order number of the first laser beam subtracts the product of the modulation frequency $f_2$ and the order number of the second laser beam. The minimum value of the difference between this result and the arbitrary multiple of the laser repetition rate of $f_2$ is the beating frequency." The beating of the laser beam has a pure sinusoidal waveform on the beam envelop. "$f_1$" and "$f_2$" refer respectively to the modulation frequency of the first and second light modulation module 102.

In one embodiment of the present disclosure that uses the loss modulation technique, the light modulation module(s) 102 is an acoustic optical modulator (AOM). The modulation frequencies of the two AOMs are $f_1$ and $f_2$, respectively. When only one AOM is used, $f_2=0$. The repetition rate of the laser beam is $f_R$. When a beam arm passes through an AOM, it absorbs phonons with a frequency determined by the AOM. The frequency spectrum of the beam arm is hence shifted, and the frequency shift is equal to the frequency of the phonons. When two beam arms with different frequency shifts are recombined collinearly, spatially, and temporally, the fundamental frequency, $\Omega(f_1, f_2, f_R)$, is produced, which corresponds to the AOM diffraction order. The simple calculation is as follows.

$$\Omega(f_1, f_2, f_R) = |f_1 - f_2|$$

(Both beams are in the $+1^{st}$ or $-1^{st}$ order diffraction.)

$$\Omega(f_1, f_2, f_R) = |f_1 - f_R|$$

(The first beam is in the $\pm 1^{st}$ order diffraction, and the second beam is in the $0^{th}$ order diffraction.)

$$\Omega(f_1, f_2, f_R) = |f_1 + f_2 - 2f_R|$$

(One beam has $+1^{th}$ order diffraction, and the other beam has $-1^{st}$ order diffraction.)

In one embodiment of the present disclosure that uses the single light amplitude modulation technique, as shown in FIG. 4, the light modulation module 102 is operated in a chopping/normal mode to amplitude modulate the laser beam for pure sinusoidal modulation. The light modulation module 102 is supplied with pure sinusoidal input signals from an external function generator 1046, so that the frequency of the light modulation module is equal to that of the input source. A laser beam emitted from the pulsed light source 101 passes through the light modulation module 102 directly, the amplitude of the laser beam is modulated by a pure sinusoidal waveform. Note that the fundamental frequency of the sinusoidal waveform is determined by the external function generator 1046. The frequencies of the light modulation module may be adjusted by a controller 1023.

Figure 4A:
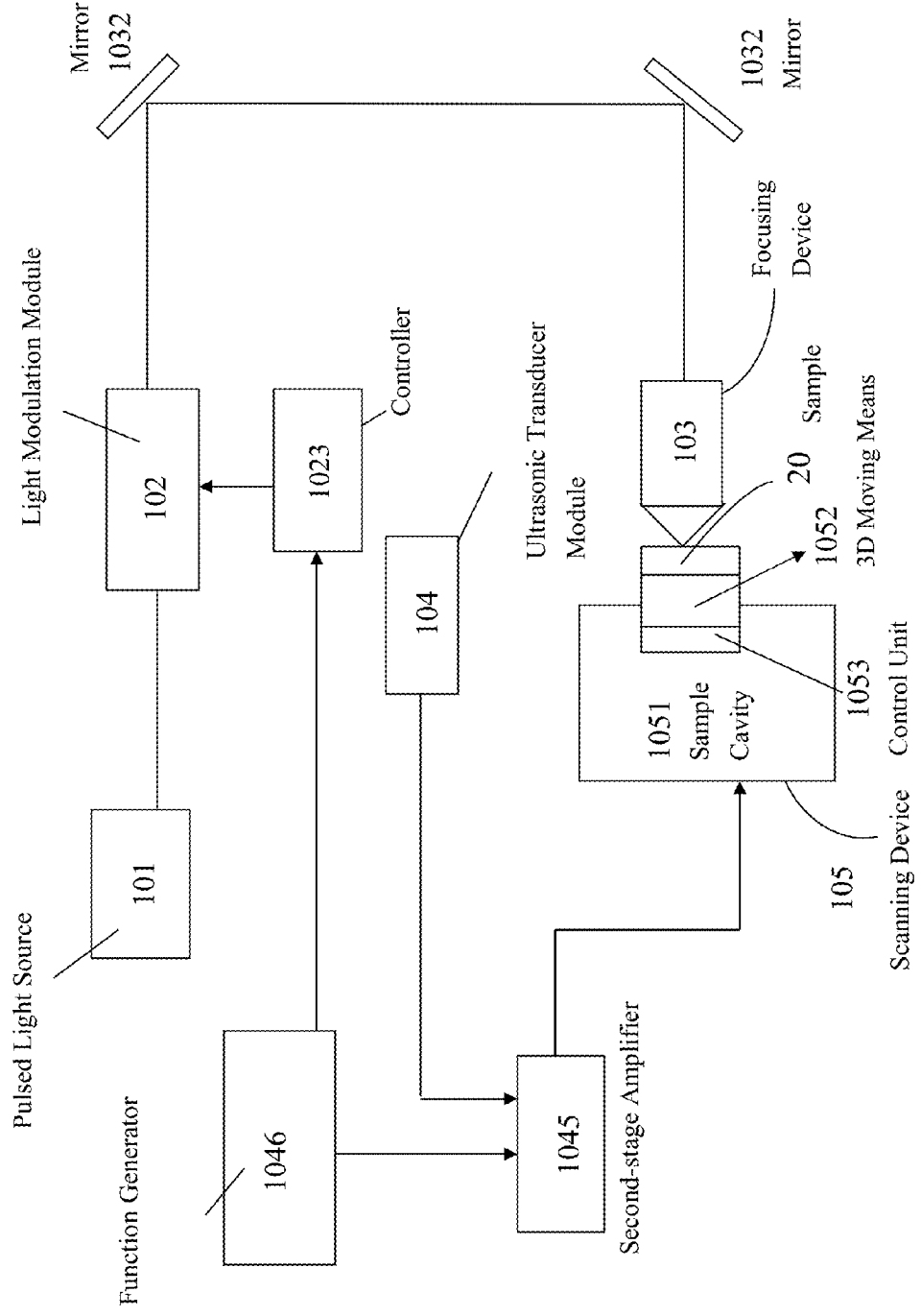
FIG. 4A and FIG. 4B are block diagrams of an optical microscopy system according to embodiments of the present disclosure using a single light amplitude modulation technique.

As shown in FIG. 4A, some embodiments of the present disclosure using the single light amplitude modulation technique comprises an ultrasonic transducer module 104 which has a frequency response covering only the desired harmonics of the fundamental frequency, and the fundamental frequency and all other harmonics are excluded from the response region. In these embodiments, the laser beam passes through a focusing device 103 for photoacoustic excitation and the ultrasonic transducer module 104 serves as a frequency filter to extract specific photon absorption photoacoustics.

As shown in FIG. 4A, some embodiments of the present disclosure using the single light amplitude modulation technique comprises an ultrasonic transducer module 104 having a wide frequency response covering multiple harmonic frequencies and a second-stage amplifier 1045 for receiving and narrow band detection of the frequency signals of the initial electrical signals (f or 2f). An electrical signal is fed from the external functional generator 1046 to the second-stage amplifier 1045 as a reference.

One embodiment of the present disclosure using the single light amplitude modulation technique further comprises a first-stage amplifier.

Figure 4B:
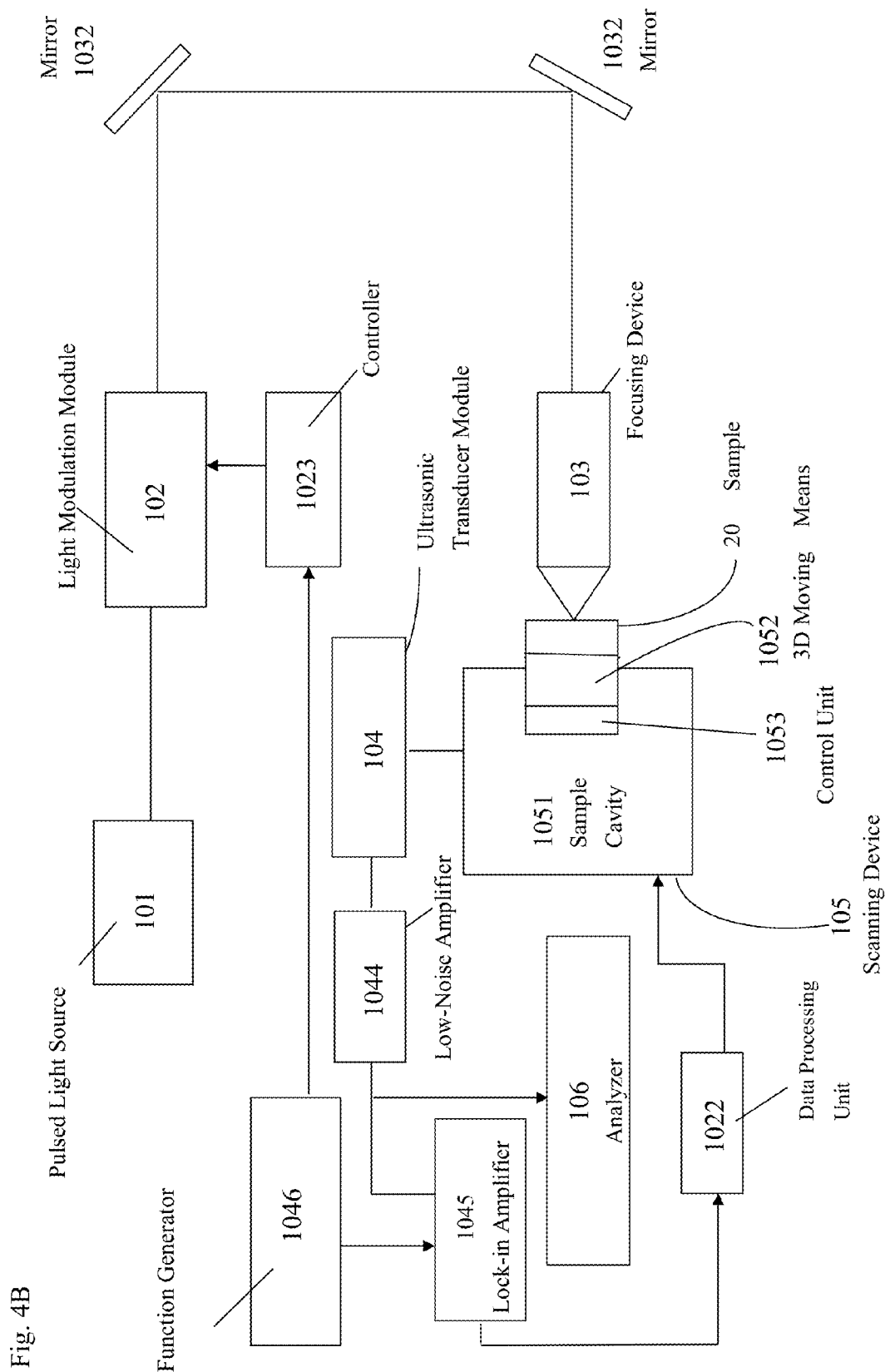

In one embodiment of the present disclosure using the single light amplitude modulation technique, the first-stage amplifier 1044 is a preamplifier. As shown in FIG. 4B, in other embodiments of the present disclosure, a plurality of amplifiers may be used. Such amplifiers include, but are not limited to, low noise preamplifiers, high linear preamplifiers, optical spectrum analyzers, or radio frequency spectrum analyzers. In one embodiment of the present disclosure using the single light amplitude modulation technique, the second-stage amplifier 1045 is a lock-in amplifier. In other embodiments of the present disclosure, a plurality of amplifiers may be used. Such amplifiers include, but are not limited to, frequency analyzing means, or scilloscopes.

In embodiments of the present disclosure that use the loss modulation technique, the fundamental frequency (the beating frequency or the sinusoidal waveform frequency) is determined by the repetition rate of the laser beam and the modulation frequencies of the light modulation modules 102. The fundamental frequency may be adjusted by changing the diffraction order or the modulation frequency of the light modulation module 102. When the light modulation module 102 is of a tunable type, the modulation frequency may be changed by adjusting the input radio frequency (RF) signal by the controller of the light modulation module. In embodiments of the present invention that use the single light amplitude modulation, where the light modulation module 102 operates in the chopping/normal mode, the fundamental frequency is determined solely by the input RF signal of the light modulation module 102. The fundamental frequency may be adjusted simply by adjusting the input RF signal.

In embodiments of the present disclosure, the modulated laser beam or the recombined laser beam passes through a focusing device 103 to be focused onto a sample 20. After passing through the focusing device 103, the modulated laser beam which is focused onto a sample 20 remains to have a pure sinusoidal waveform on the beam envelop. In one embodiment of the present disclosure, the focusing device 103 is an objective lens. In other embodiments of the present disclosure, a plurality of focusing device may be used. Such focusing devices include, but are not limited to, microscopic objective lenses, lenses, mirrors, spherical mirrors, parabolic mirrors, phase modulation grids, grin rods, the arc surface at the terminal of optical fibers, or any objects that can produce focused illumination on a sample.

To improve signal intensity and signal-to-noise ratio (SNR), embodiments of the present disclosure employ contrast agents to cause or enhance nonlinear photoacoustic effect. As a result, the spectrum sensitivity and frequency selectivity of the present disclosure are improved because various wavelength excitation responses are triggered or enhanced and rich optical contrasts are provided. Two types of contrast agents may be used: endogenous contract agents and exogenous agents. When a particular sample itself has the capability of being excited to produce nonlinear photoacoustic effect, the sample itself may serve as endogenous contrast agents. The contrast agents comprise fluorescent dyes, organic dyes, nanoparticles, micro-particles, core-shell particles, chemicals, bio-target nucleic acids, proteins, bio-medicines, bio-cells, hemoglobin, melanin, or a combination thereof. The contrast agents usually have wide energy band structures, resonant energy states, or carrier transferring mechanisms to cause or enhance efficient conversion of the optical energy into an ultrasonic (acoustic) wave.

In one embodiment of the present disclosure, the contrast agent is a mixture of fluorescent dye molecules and carbon particles. When the carbon particles capture the fluorescent dye molecules and the carbon particles have a wide energy-band structure, the particles become an intermediary agent to transfer the two-photon fluorescence into two-photon photoacoustic ultrasound. When the incident light induces two-photon absorption of the fluorescent dye molecules, some of the energy is transferred into fluorescence, while the rest of energy, with the help of energy levels of the carbon particles, is transferred into phonon vibration. With the photoacoustic contrast agents, two-photon photoacoustic ultrasound may be generated more efficiently.

As shown in FIG. 5A, a dye-particle mixture may be used to increase the intensity of two-photon photoacoustic signals. The icon "•" denotes fluorescent dye molecule, and the icon "⊙" denotes carbon particle. When fluorescent dye molecules are illuminated by a pulsed laser beam, the absorbed laser light energy is transformed into two photon fluorescence. When carbon particles are illuminated by a pulsed laser beam, the absorbed laser light energy is transformed into particle vibration, which generates a single photon absorption photoacoustic wave. When the dye-particle mixture is illuminated by a pulsed laser beam, the dye-particle mixture transfers the laser light energy absorbed by the fluorescent dye molecules to the carbon particles which release the energy through particle vibration, a non-radiative relaxation. This non-radiative relaxation then generates a two photon absorption photoacoustic wave. FIG. 5B shows the energy band structure of the fluorescent dye molecules and the carbon particles.

One embodiment of the present disclosure using the single light amplitude modulation technique comprises a first-stage amplifier 1044 and a second-stage amplifier 1045, as shown in FIG. 4B. The electrical signals are pre-amplified by the first-stage amplifier 1044. The first-stage amplifier 1044 is connected to a second-stage amplifier 1045 which is used for signal demodulation. The demodulation occurred in the second-stage amplifier is narrow-band frequency detection with long time integration (with external frequency reference). By changing the harmonics of the external frequency reference, different orders of the fundamental frequency within the electrical signals are detected with high sensitivity.

Figure 6:
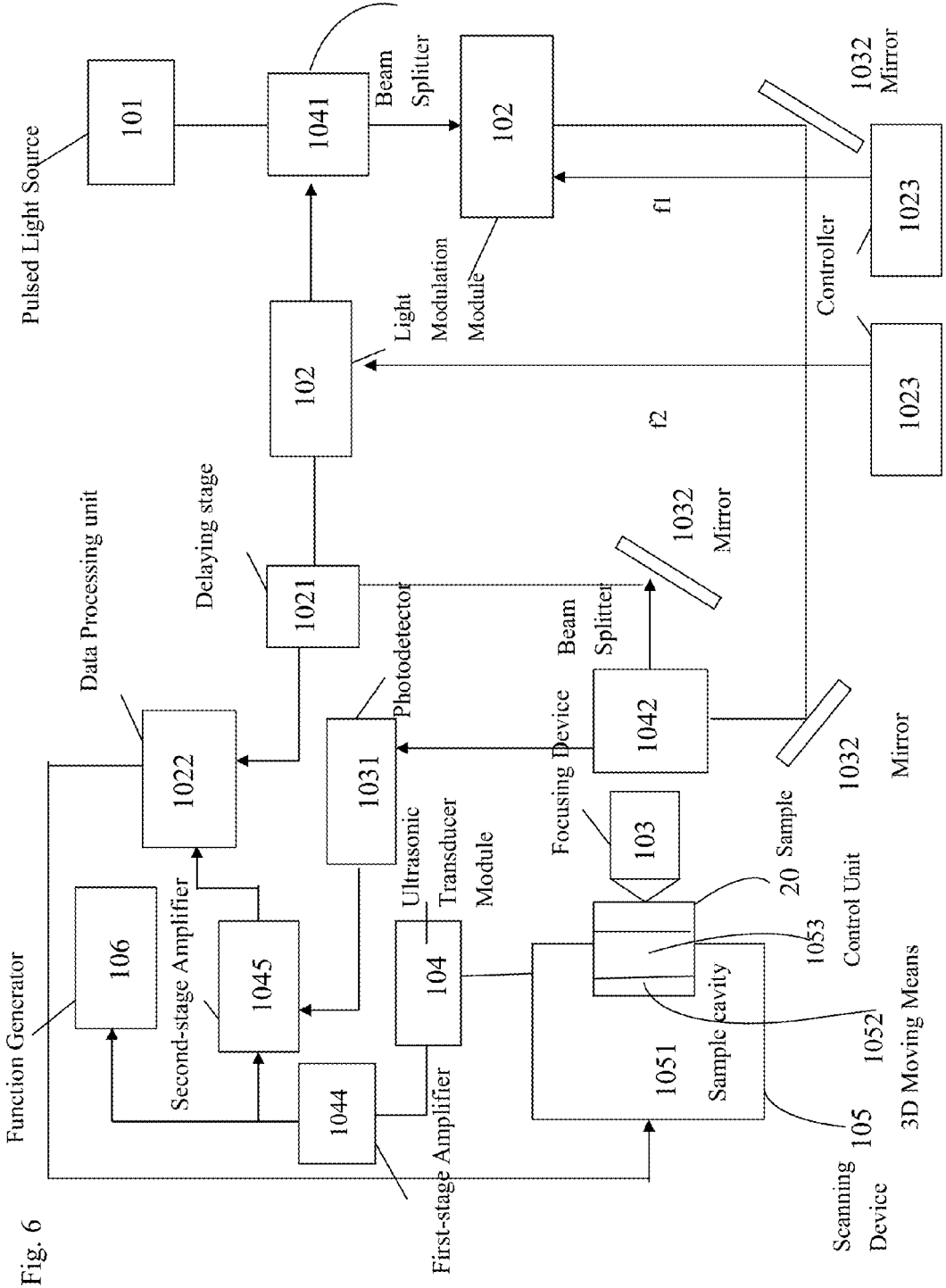
FIG. 6 is a block diagram of an optical microscopy system according to the first example of the present disclosure.

One embodiment of the present disclosure using the loss modulation technique comprises a first-stage amplifier 1044, a second-stage amplifier 1045, and a photodetector 1031, as shown in FIG. 6, there are two recombined beams from the beam splitter 1042. One beam is for photoacoustic excitation, while the other one is detected with a photodetector 1031, which transforms the light into a photodetective signal and send this photodetective signal as a reference to the second stage amplifier 1045. Electrical signals are pre-amplified by the first-stage amplifier 1044. The first-stage amplifier 1044 is connected to a second-stage amplifier 1045 which is used for signal demodulation. The demodulation occurred in the second-stage amplifier is narrow-band frequency detection with long time integration (with external frequency reference). By changing the harmonics of the external frequency reference, different orders of the fundamental frequency within the electrical signals are detected with high sensitivity.

In one embodiment of the present disclosure, the ultrasonic transducer module 104 further comprises an analyzing unit 106 for sweeping the frequency spectrum of the initial electrical signal or the signals amplified by the first-stage amplifier. The analyzing unit 106 is capable of analyzing the fundamental frequency (f), second harmonics of the fundamental frequency (2f), and/or multi-harmonics of the fundamental frequency (n f, n>–3) of electrical signals transformed by the ultrasonic transducer module 104.

One embodiment of the present disclosure further comprises a data processor for advanced image processing. The data processor may be a computer, a data recorder, a computing unit or equivalent.

In one embodiment of the present disclosure, the scanning device 105 configured and positioned to move the sample further comprises (a) a sample cavity 1051 for loading the sample; (b) a three-dimensional moving means 1052. i.e., 3D device or 3D translation stage, for moving the sample around for scanning; and (c) a controlling unit 1053 for controlling the three-dimensional moving means. The three-dimensional moving means may be a two-axis moving platform or a three-axis moving platform.

In one embodiment of the present disclosure, the scanning device 105 configured and positioned to move the focused laser beam further comprises (a) a 2 D light scanner for scanning the laser light; and (b) a controlling unit for controlling the 2 D light scanner. The 2D light scanner may be a micro-electromechanical system (MEMS), a nano-electromechanical system (NEMS), or a Galovo mirror.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention.

EXAMPLES

The examples below are non-limiting and are merely representative of various aspects and features of the present invention.

In the first example of the present disclosure, the fundamental frequency of the laser beam, which was amplitude modulated for pure sinusoidal modulation by using a loss modulation technique, was 500 kHz. By detecting the fundamental frequency and the harmonics of the fundamental frequency, 500 kHz and 1 MHz, images derived from single-photon and two-photon-absorption-induced photoacoustic effect were obtained.

As shown in FIG. 6, the pulsed light source 101 was a femtosecond laser (Tsunami Ti:Sapphire Laser, 800 nm femtosecond laser, pulse width ~100 fs, repetition rate 80 MHz). Two acoustic optical modulators (AOMs) (Neos Technologies, 23080-3-.85-LTD) 102 were operated in CW mode and their modulation frequencies were adjusted by two controllers 1023 to be slightly different, 80.5 MHz and 81 MHz, respectively. A laser beam emitted from the pulsed light source 101 passed through a beam splitter 1041 which split the laser beam into two beam arms. Each beam arm individually and separately passed through one of the two AOMs 102. One of the light paths was adjusted via a delay stage 1021 to ensure the travel distances of these two beam arms were the same. These two beam arms were recombined again via the second beam splitter 1042, and the recombined beam was amplitude modulated to have a pure sinusoidal waveform on its envelope. The fundamental frequency, 500 kHz, was the difference of the modulation frequencies of the two AOMs 102. There were two recombined beams from the beam splitter 1042. One beam was for photoacoustic excitation, while the other one was detected by a photodetector 1031, which transformed the light into an electrical signal and sent this signal as a reference to the second-stage amplifier 1045.

Figure 7:
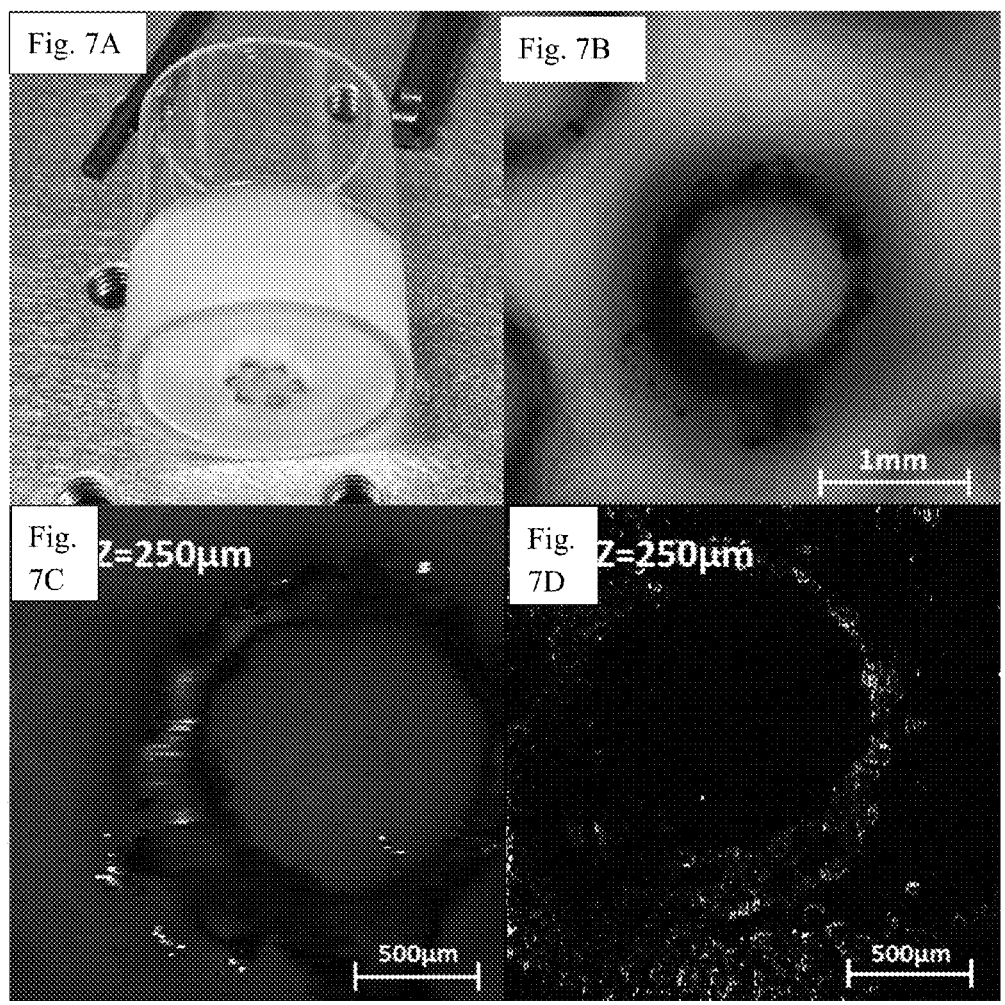
FIG. 7A is a photograph of the phantom tissue to be imaged.
FIG. 7B is an image of the phantom tissue under a conventional optical microscope.
FIG. 7C and FIG. 7D are single-photon photoacoustic image and two-photon photoacoustic image, respectively.

An objective lens 103 (Olympus MPLFLN 50×, working distance 15 mm. 0.45 NA) was used to focus the recombined beam onto a homemade sample 20. A layer of agar gel (2.5~4 wt %) was used as the phantom tissue. In order to achieve ultrasonic collection depth, another thick layer of agar gel (7 mm) was placed on top of the original pattern. The photograph of the cavity, the pattern, and the phantom design is shown in FIG. 7A. The image of the pattern under a microscope is shown in FIG. 7B. In order to demonstrate the optical-scanning imaging, small donut shape patterns (3 mm thick) were created to be filled with contrast agents by a capillary tube (with 1.5 mm inner diameter and 1.8 mm outer diameter) at the bottom of the sample cavity 1051. The pattern dimension was similar to the ultrasonic wavelength ($\lambda_{US}$=1.5 mm at 1 MHz). The sample cavity 1051 was set on a 3D translation stage 1052 driven by a controlling unit 1053 (Newport MM3000, Motion Controller) During the experiment, the cavity was filled with deionized water. The exogenous contrast agents were produced by mixing WKP-1 (extracted from highlighters (Zebra, Liberty Stationery Corp. It was supplied by a local stationary store.), a dye having the property of two-photon fluorescence, with Wu-Zhu Calligraphy Paints, a dilute carbon solution. The objective lens 103 and the ultrasonic transducer module 104 (an immersion-type ultrasonic transducer, Olympus V303) were assembled in the transmissive mode. The immersion-type ultrasonic transducer was protected from direct light illumination by the light blocking effect of the agar gel due to its strong scattering. The photoacoustic contrast agents were excited by the modulated laser beam causing two-photon absorption which generated an acoustic wave. The contrast agent produced two types of photoacoustic waves. Theoretically, when the contrast agent absorbed single photon at one time (i.e., linear absorption), it would emit a photoacoustic wave at 500 kHz. When the contrast agent absorbed two photons simultaneously (i.e., nonlinear absorption), it would contribute to the photoacoustic wave at 1 MHz. The detected 500 kHz was the fundamental frequency whereas the detected 1 MHz signal was the second harmonics of the fundamental frequency.

The immersion-type ultrasonic transducer 104 was then used to transform the detected acoustic wave into an electrical signal. The immersion-type ultrasonic transducer 104 was connected to a low-noise preamplifier 1044 (Olympus PR5660B) to avoid electronic nonlinear effects caused by electronic devices. Finally, a lock-in amplifier 1045 (Stanford Research System SR844) was connected to the preamplifier 1044 for narrow band detection of multi-harmonics of the fundamental frequency. Long time integration was applied to eliminate random noises. The signal intensity of the multi-harmonics of the fundamental frequency at each point was transferred to the recording part of the scanning device 105 (Newport MM3000, Motion Controller) to create a 2D image. A single-photon and a two-photon photoacoustic images of the phantom tissue were obtained as shown in FIGS. 7C and 7D, respectively.

Figure 8:
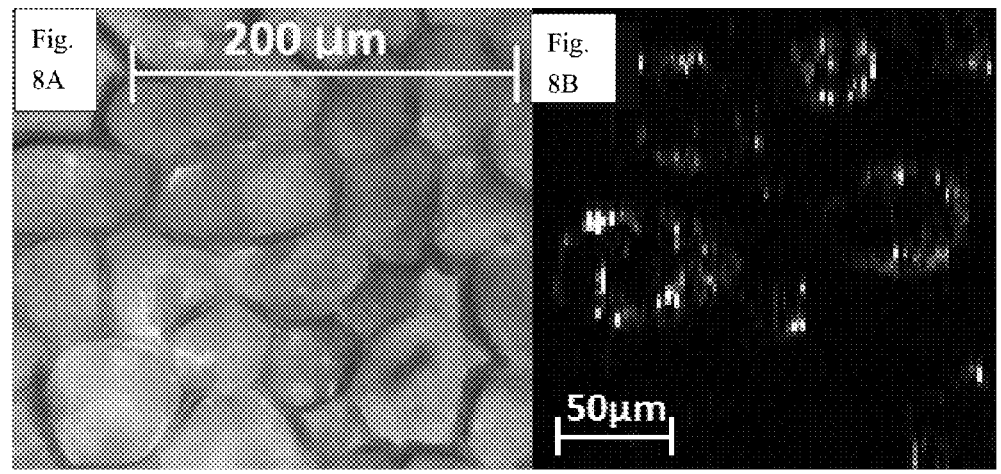
FIG. 8A is an image of a leaf tissue recorded by an optical microscopy system according to the second example of the present disclosure.
FIG. 8B is an image of the leaf tissue recorded by an optical wide field microscope.

In the second example of the present disclosure, all conditions were controlled to be the same as the first example. The sample to be imaged was a leaf tissue treated with the same exogenous photoacoustic agent, a mixture of the fluorescent dye-carbon particle. The leaf tissue was then placed under a 1 mm layer of agar gel (2.5-4 wt %). As shown in FIG. 8A, high contrast ratio was found on the edge of the leaf cell because the cell wall absorbed most of the contrast agent and generated strong two-photon photoacoustic signals. Theoretically, images of the leaf cell's inner structure could also be recorded if the contrast agent was ingested into the cell by using a lipid-based coating technique. The maximum penetration depth of the imaging system was approximately 1 millimeter according to the thickness of the agar gel layer and the spatial resolution was approximately 10 micrometers. For comparison purposes, FIG. 8B is an image of the same leaf tissue under a conventional bright-field microscope.

Figure 9A:
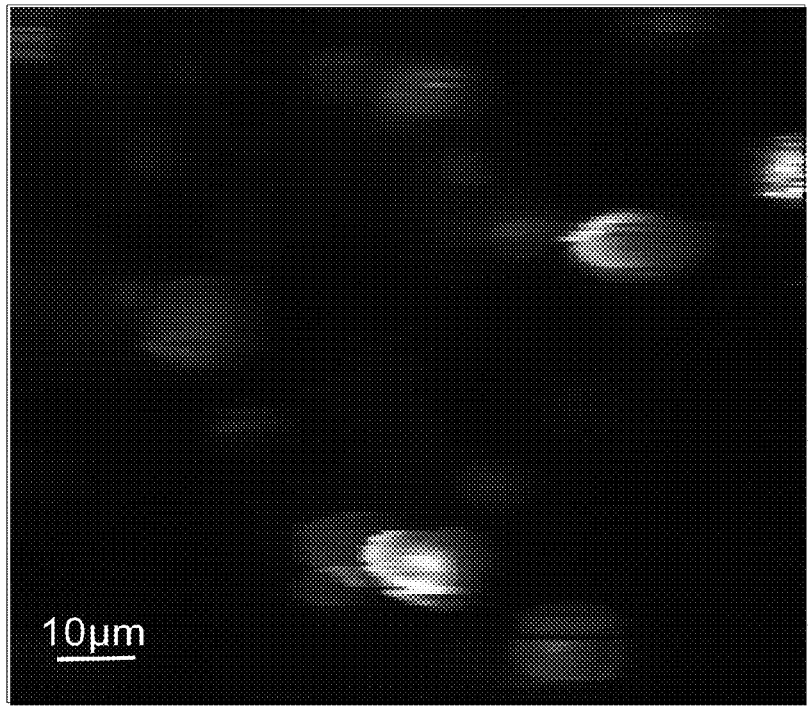
FIG. 9A is a photoacoustic image of a leaf tissue from multi-photon absorption recorded by an optical microscopy system according to the third example.
Figure 9B:
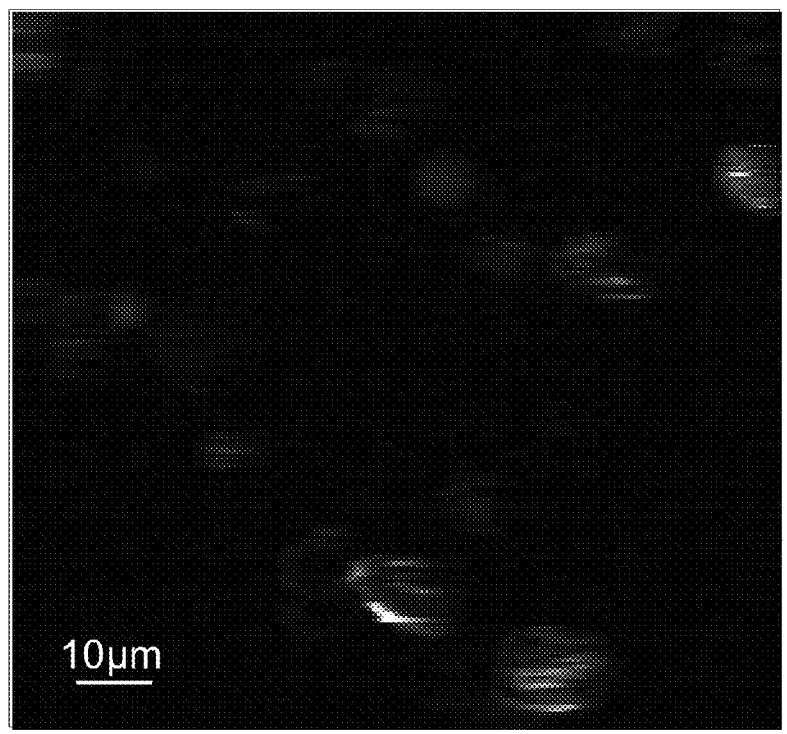
FIG. 9B is an photoacoustic image of a leaf tissue from single-photon absorption.

The third example of the present disclosure followed the same procedures and was performed under the same conditions as the first example except that the focusing device 103 was Olympus MPLFLN 10× (working distance 11 mm, 0.3 NA) and the exogenous contrast agent was a solution of Rhodamine B (Sigma Aldrich) in Methanol (0.1M). A piece of leaf tissue was treated with the contrast agent and examined under a microscope. The leaf tissue was then buried beneath the agar phantom, with 1 mm agar layer between the leaf tissue and the bottom of the cavity 1051. Images of the leaf tissue were obtained by using a three-dimensional moving device 1052 (Newport Motion Controller MM 3000) for 2D raster scanning of microscopic spots. FIG. 9A and FIG. 9B are the photoacoustic images of the same leaf tissue from single photon absorption and multi-photon absorption, respectively. The resolution was approximately 1 μm.

What is claimed is:
1. An optical microscopy system comprising:
  (a) a pulsed light source configured to emit at least one laser beam;

(b) at least one light modulation module configured to modulate in amplitude the at least one laser beam for pure sinusoidal modulation;

(c) a focusing device configured to focus the at least one modulated laser beam onto a sample, wherein the sample itself is an endogenous contrast agent or is treated by at least one exogenous contrast agent so as to be excited to generate nonlinear photoacoustic waves in the sample in response to the at least one modulated laser beam;

(d) at least one ultrasonic transducer module configured to receive and transform the nonlinear photoacoustic waves into electrical signals and to extract frequency signals within the electrical signals; and (e) a scanning device configured to scan, record, map, and process intensity of the signals received from the at least one ultrasonic transducer module to create images of the sample.

2. The optical microscopy system as claimed in claim 1, wherein the scanning device comprises a 3D scanning stage for 2D or 3D imaging and a data processing unit to record and process intensity of the signals received from the at least one ultrasonic transducer module and to synchronize the 3D scanning stage and the at least one ultrasonic transducer module.

3. The optical microscopy system as claimed in claim 1, wherein the pulsed light source is a femtosecond or picosecond.

4. The optical microscopy system as claimed in claim 1, wherein at least one of the light modulation modules is an acousto-optical modulator (AOM).

5. The optical microscopy system as claimed in claim 1, wherein a modulation frequency of the at least one light modulation module is adjustable.

6. The optical microscopy system as claimed in claim 1, wherein the at least one light modulation module is configured and operated in a continuous wave (CW) mode for applying a loss modulation technique.

7. The optical microscopy system as claimed in claim 6, further comprising a delay stage for adjusting travel distance of the at least one laser beam.

8. The optical microscopy system as claimed in claim 6, further comprising a first-stage amplifier, being connected to the at least one ultrasonic transducer module for amplifying initial electrical signals received from the at least one ultrasonic transducer module, and a second-stage amplifier, being connected to the first-stage amplifier, for receiving and narrow band detection of the frequency signals of the initial electrical signals.

9. The optical microscopy system as claimed in claim 8, wherein the second-stage amplifier is a lock-in amplifier.

10. The optical microscopy system as claimed in claim 8, further comprising a photodetector for transforming the at least one laser beam into photodetector signal and sending the photodetector signal as a reference to the second-stage amplifier.

11. The optical microscopy system as claimed in claim 8, wherein the first-stage amplifier is a preamplifier.

12. The optical microscopy system as claimed in claim 1, further comprising an external function generator connecting to the at least one light modulation module, wherein the at least one light modulation module is configured and operated in a chopping/normal mode for applying a single light amplitude modulation technique.

13. The optical microscopy system as claimed in claim 1, wherein the focusing device is an objective lens.

14. The optical microscopy system as claimed in claim 13, wherein the scanning device further comprises (a) a sample cavity for loading the sample; (b) a three-dimensional moving means for moving the sample around for scanning; and (c) a controlling unit for controlling the three-dimensional moving means.

15. The optical microscopy system as claimed in claim 1, wherein the focusing device and the at least one ultrasonic transducer module are assembled on a same side in a reflection mode, on an opposite side in a transmissive mode, or by a side in an orthogonal mode.

16. The optical microscopy system as claimed in claim 1, wherein the at least one ultrasonic transducer module is an immersion-type ultrasonic transducer.

17. The optical microscopy system as claimed in claim 16, wherein the scanning device further comprises (a) a 2D light scanner and (2) a controlling unit for controlling the 2D light scanner.

18. The optical microscopy system as claimed in claim 1, wherein the scanning device is configured and positioned to move the sample.

19. The optical microscopy system as claimed in claim 1, wherein the scanning device is configured and positioned to move the focused laser beam.

20. The optical microscopy system as claimed in claim 1, further comprising a data processor for advanced image processing.

* * * * *